US009060705B2

(12) United States Patent
Holzhacker et al.

(10) Patent No.: US 9,060,705 B2
(45) Date of Patent: Jun. 23, 2015

(54) ELECTRODE ASSEMBLY FOR ELECTRICAL IMPEDANCE TOMOGRAPHY

(75) Inventors: Albert Holzhacker, Sao Paulo (BR); Stephan H. Boehm, Hamburg (DE); Diogo Moretti Branchini, Campinas (BR)

(73) Assignees: Autopoiese Participacoes, LTDA, São Paulo (BR); Timpel, S/A, São Paulo-SP (BR)

( * ) Notice: Subject to any disclaimer, the term of this patent is extended or adjusted under 35 U.S.C. 154(b) by 1267 days.

(21) Appl. No.: 12/094,571

(22) PCT Filed: Dec. 19, 2006

(86) PCT No.: PCT/BR2006/000284
§ 371 (c)(1),
(2), (4) Date: Nov. 18, 2008

(87) PCT Pub. No.: WO2007/070997
PCT Pub. Date: Jun. 28, 2007

(65) Prior Publication Data
US 2009/0084674 A1    Apr. 2, 2009

(30) Foreign Application Priority Data

Dec. 20, 2005 (BR) ..................................... 0505736
Oct. 10, 2006 (BR) ..................................... 0604479

(51) Int. Cl.
*A61B 5/053* (2006.01)
*A61B 5/00* (2006.01)

(52) U.S. Cl.
CPC .............. *A61B 5/0536* (2013.01); *A61B 5/6823* (2013.01); *A61B 2560/0443* (2013.01);

(Continued)

(58) Field of Classification Search
CPC .. A61B 5/04085; A61B 5/053; A61B 5/0536; A61B 5/6823; A61B 5/6831; A61B 2560/0443; A61B 2562/043; A61B 2562/08; A61B 2562/164
USPC .................. 600/382, 386, 390, 393, 509, 547
See application file for complete search history.

(56) References Cited

U.S. PATENT DOCUMENTS 4,391,279 A * 7/1983 Stein ............................ 600/387
4,638,807 A * 1/1987 Ryder ........................... 600/383
(Continued)

FOREIGN PATENT DOCUMENTS

JP          2000139866 A      5/2000
JP          2000175875 A      6/2000
(Continued)

OTHER PUBLICATIONS

Woo E J et al., "Finite-Element Method in Electrical Inpedance Tomograpphy", Medical and Biological Engineering and Computing, Springer, Heildelberg, DE, vol. 32, No. 5, (1994), pp. 530-536.

*Primary Examiner* — Lee S Cohen
*Assistant Examiner* — Erin M Cardinal
(74) *Attorney, Agent, or Firm* — TraskBritt (57) ABSTRACT

An electrode assembly for electrical impedance tomography comprising a plurality of different electrode modules, each containing a support strap made of a flexible material that presents a reduced longitudinal deformability and carrying a predetermined number of electrodes, each support strap being dimensioned to be seated and retained onto a respective extension portion of a body segment of a patient. Each electrode module presents the number of electrodes and a distance "De" between each two consecutive electrodes predetermined as a function of a specific operational pattern to be obtained from each electrode module. The assembly can further comprise an electrical conducting cable having an end connected to a monitoring apparatus and a free end provided with a connector to be coupled to a respective electrode of an electrode module.

23 Claims, 10 Drawing Sheets

(52) U.S. Cl.
CPC .............. *A61B 5/417* (2013.01); *A61B 5/6831* (2013.01); *A61B 5/6833* (2013.01); *A61B 2562/0209* (2013.01); *A61B 2562/043* (2013.01); *A61B 2562/08* (2013.01)

(56) References Cited

U.S. PATENT DOCUMENTS

| | | | |
|---|---|---|---|
| 4,649,932 A | 3/1987 | Smith | |
| 4,928,696 A * | 5/1990 | Henderson et al. | 600/383 |
| 5,184,624 A | 2/1993 | Brown et al. | |
| 5,313,952 A * | 5/1994 | Hoch | 600/390 |
| 5,341,806 A * | 8/1994 | Gadsby et al. | 600/393 |
| 5,518,007 A * | 5/1996 | Becker | 600/390 |
| 6,510,340 B1 * | 1/2003 | Jordan | 600/544 |
| 7,158,822 B2 * | 1/2007 | Payne, Jr. | 600/390 |
| 7,283,869 B2 * | 10/2007 | Onda et al. | 600/547 |
| 2003/0176808 A1 * | 9/2003 | Masuo | 600/547 |
| 2004/0236202 A1 | 11/2004 | Burton | |
| 2004/0260167 A1 | 12/2004 | Leonhardt et al. | |
| 2005/0070778 A1 * | 3/2005 | Lackey et al. | 600/366 |
| 2005/0107719 A1 * | 5/2005 | Arad | 600/547 |
| 2006/0058600 A1 | 3/2006 | Eichler | |
| 2006/0084855 A1 * | 4/2006 | Teschner et al. | 600/390 |
| 2007/0007973 A1 * | 1/2007 | Matthiessen et al. | 324/692 |
| 2007/0027402 A1 * | 2/2007 | Levin et al. | 600/547 |
| 2007/0135721 A1 * | 6/2007 | Zdeblick | 600/508 |
| 2013/0053674 A1 * | 2/2013 | Volker | 600/389 |

FOREIGN PATENT DOCUMENTS

| | | |
|---|---|---|
| JP | 2002369806 A | 12/2002 |
| JP | 2003339658 A | 12/2003 |
| JP | 2005531386 A | 10/2005 |
| RU | 2127075 C1 | 3/1999 |
| WO | 2004/021880 | 3/2004 |

* cited by examiner

ELECTRODE ASSEMBLY FOR ELECTRICAL IMPEDANCE TOMOGRAPHY

CROSS-REFERENCE TO PRIOR APPLICATIONS

This application is the U.S. National Phase of International Application No. PCT/BR2006/000284, filed Dec. 19, 2006, which claims priority from Brazilian Patent Application No. PI0505736-1, filed Dec. 20, 2005 and Brazilian Patent Application No. PI0604479-4, FILED Oct. 10, 2006. The disclosures of each application is incorporated herein by reference in their entirety. The International Application published in English on Jun. 28, 2007 as WO 2007/070997 under PCT Article 21(2).

FIELD OF THE INVENTION

The present invention is related to the provision of electrode modules, each containing a plurality of electrodes to be applied around a body segment of a human patient or an animal, in order to carry out the Electrical Impedance Tomography (EIT).

BACKGROUND OF THE INVENTION

The Electrical Impedance Tomography (EIT) allows visualizing and monitoring a cross-section of parts of the human body, by capturing its electrical potential. An electrical current around the surface is conducted inside the body in a rotative pattern, generating a gradient of electrical potential on the surface. The electrical impedance distribution measured in the body parts is transformed, with the help of an image reconstruction algorithm, in a two-dimensional image. For this reason, the EIT has a great potential to be used in the medical field, mainly for image visualization in real-time of the cardiopulmonary functions, for example, in situations in which patients need to be ventilated or have suffered an accident, trauma, etc.

A typical biomedical EIT apparatus utilizes the concept of placing a plurality of equidistantly spaced electrodes, surrounding totally one part of the body. Generally, in the monitoring system it is necessary to precisely place the 16 to 32 electrodes around the desired surface. Since the use of multiple electrodes is needed, it is difficult to precisely place the electrodes one-by-one around the body, mainly in an equidistant form and in the same cross-section. Furthermore, it is a laborious process that requires time, attention and skilled personnel.

A solution for the problem above makes use of an elastic belt with electrodes. The basic idea of the electrode belt is to install a plurality of electrodes in an elastic material. In this way, the placement of the electrodes around a body would be quick and the elastic material would provide equidistant electrodes, at the same time. However, it is difficult to guarantee an equidistant position of the electrodes by using an elastic material. Furthermore, to avoid the electrodes from moving on the body during the data acquisition, this belt has to be tightly placed on the desired surface. Accordingly, this elastic force applied to the surface of the thorax can provoke scabs and make breathing difficult. For an adequate fixation of the belt it is necessary to provide several belt sizes due to, for example, the existence of several thorax perimeters, which generates a high cost inventory and the necessity of a large stock. Another problem is the possibility of occurring bad contact of the electrodes with the external part of the body under observation, due to the existence of different thorax anatomies, which problem cannot be solved by using an elastic material. Such differences occur as a function of the sex and muscular structure of the patient, for example, male patients who have large chest muscles present a depression in the middle of the chest and, similarly, in the middle of the back as a consequence of the muscular structure of the back; in women, there are anatomical variations of the thorax, mainly regarding the different breast sizes.

Situations that require discontinuity in the electrode line around the thorax, or situations that do not allow the electrodes to totally surround the body, cannot be monitored by the current EIT systems, such as, for example, post-operative period of cardiac surgeries, lesions caused by side arms or firearms, burns, skin lesions that result in bloody areas due to dermatological or infectious diseases, or a situation in which there is no access to a part of the body, for example, when the victim is trapped in the accident site or has injured the spinal cord, making difficult or even impeding his/her movement.

Moreover, the present state of the art does not allow optimizing the image resolution and definition in a region of interest. For example, U.S. Patent Application 2004/0260167 A1 describes an electrode elastic belt that can be formed by joining belt segments, the segments presenting the same number of electrodes that can be equally spaced from each other. In accordance with the teachings of the document above, the formation of the electrode belt in multiple interconnected segments connected presents the advantage of reducing the number of electrical conducting cables disposed along the belt, besides leading to a quick and easy application of the electrodes to unconscious patients or that cannot be moved.

Despite the benefits regarding facility of application and reduction of the extension of the conducting cables along the electrode belt, this prior art solution proposes an electrode distribution surrounding totally a body segment, making impossible its use in situations in which the electrode belt has to be interrupted in one or more regions of the body segment.

Due to the constructive form of the electrode elastic belt, it is not possible to provide concentration of electrodes in specific regions, that is, an irregular electrode distribution, aiming at obtaining images with higher definition in certain areas if interest, even in situations in which the electrode belt has to be interrupted in one or more regions of the body segment.

SUMMARY OF THE INVENTION

The present invention has a different approach for the problem. Instead of focusing a way of placing the electrodes equidistantly and totally surrounding an object defined by a body segment of a human patient or an animal, an EIT apparatus has been developed which allows both planning and informing the relative position of the electrodes. Thus, this apparatus permits the use of a variable number of electrodes and of spacings and it may be utilized in situations in which there is also a discontinuity in the electrode line, besides not requiring to place the electrodes around the entire external contour of a body segment being analyzed.

The main object of the present invention is to provide an assembly of electrodes arranged in modules which can be applied, in a practical and precise manner, to different thorax shapes and perimeters, such as of newborn children, children adults and animals.

Another object of the present invention is to provide an electrode assembly in modular arrangement, as mentioned above, with a small number of parts that are capable of covering a broad variation of morphological characteristics of the body segments to be analyzed. Consequently, there is a cost reduction with stocks and the operation becomes easier. Moreover, electrode failures in a belt requires replacing the entire belt; in the case of the modular arrangement, only the worn out or defective module is replaced.

It is also an object of the present invention to provide an electrode assembly as cited above, which permits to maximize the resolution and quality of the image in regions of interest, such as: heart, right or left lung, parts subject to infection, etc., by positioning the electrodes in relation to the region of interest.

A further object of the present invention is to provide an electrode assembly as mentioned above, which permits a practical, precise and quick application, even in situations in which there are restrictions to access the perimeter of the body segment to be analyzed, for example, due to accidents, injuries, traumas or surgeries.

According to the invention, the electrode assembly comprises a plurality of different electrode modules, each comprising a support strap made of a flexible material that presents a reduced longitudinal deformability and carrying a desired number of electrodes to be electrically connected to a monitoring apparatus, one of the modules comprising at least two electrodes, each electrode module having its respective support strap dimension to be seated and retained on a respective extension portion of a body segment to be analyzed, according to a plane of interest sectioning the body segment, each of the different electrode modules presenting the number of electrodes and a distance between each two consecutive electrodes predetermined as a function of a specific operational pattern to be obtained from each electrode module.

In one embodiment, each electrode of an electrode module is electrically connected to a monitoring apparatus by means of an electrical conducting cable.

According to the invention, each electrode module comprises a certain number of electrodes disposed with a spacing between each two consecutive electrodes which can have the same value or distinct values, allowing some modules to have electrodes equally spaced apart along a median longitudinal alignment of the module, and other electrode modules to have the electrodes concentrated in one or more of the regions of the module and dispersed in others.

The constructive variations existing for the modules, regarding the number, arrangement and extension of the respective support strap, allows having a suitable module for each region of a body segment of the patient and for the resolution degree desired for this or that region.

For example, in a situation in which it is not possible to place electrode modules in the region of the right chest, a possible solution for this problem would be to place a module with 8 electrodes on the left chest and a module with 12 electrodes on the back of the patient.

The electrode assembly of the present invention has been developed to be applied in an EIT system which preferably utilizes an image reconstruction algorithm, which operates analogously as a finite element mesh, whereby the image resolution generated by EIT will be optimized by increasing the number of electrodes near the desired region. On the other hand, the lower the number of electrodes, the lower will be the image resolution generated.

Thus, the combinations of different modules permit that the EIT system be utilized in the case of a pulmonary tomography, in a more precise, practical and quick manner for any perimeter of patient, newborn children and adults and with any thorax shape, both for females and males and for different clinical situations, even those which require an interference in the electrode line.

In order to provide the correct operation of the EIT apparatus, the latter must be informed about the position of the electrodes, which can be achieved electronically through the algorithm or the identification codes present in each electrode module and through the combination of these identification codes and their respective distances. For this purpose, each electrode module can have a device for providing and indicating a precise spacing and an identification code.

The spacing device, if existing, can comprise a material with a distance graduation installed in one of the module ends. Then, the distance between the electrodes will be informed by the value indicated by the spacing system. This spacing system is a practical and simple tool which permits the correct spacing of the electrode modules. A more complex system can be made with a variable resistance installed in the spacing device. Since a variable resistance presents a specific value in ohms for each distance, then the distance between the electrodes will be determined by the value of this resistance, which can be informed by the electrode itself to the monitoring system.

The identification codes inform the characteristics of the electrode modules through numbers or a bar code, the characteristics comprising, for example, distance between the electrodes of each module, module size, the electrode arrangement (concentrated or not) in the module, and if the distances between electrodes are equal.

Consequently, these last two tools make possible to inform the monitoring system about the exact position of each electrode in relation to a point of reference on the body being examined.

The operation of the image reconstruction algorithm can be based on a finite element mesh adapted to each case in particular.

One of the aspects related to the operation of the electrode assembly of the present invention refers to the insertion of the actual electrode arrangement in the reconstruction algorithms, the arrangement being two-dimensional or three-dimensional. Except the classical back-projection algorithm, most of the image reconstruction algorithms mold the plane through a finite element mesh which represents the body section to be studied. The position of the measuring electrodes is necessarily identified, consisting in a prior information of the model. An interesting aspect of the model based on the finite element mesh is that the distance between the electrodes has to be only informed, not being necessary to be the same between all the electrodes.

The application of a greater number of electrodes allows obtaining a greater number of independent measures, leading to an increased spatial resolution of the image, which justifies utilizing a more advanced finite element mesh. As part of the present invention, it is contemplated to place a higher number of modular electrodes close to a region of interest, by selecting the most suitable electrode module.

For example, in case the priority is the cardiac monitoring, one can work with a greater number of electrodes next to the sternum, and also increase the number in other spatial planes, obtaining information in three spatial dimensions, which permits a better estimate of volumetric calculation (for example, estimate of the systolic volume in each cardiac cycle).

Another interesting aspect is to place the electrodes only in the frontal region of the thorax, this procedure being useful in situations of emergency or trauma, when the patient must not be moved, under the risk of aggravating a pre-existing marrow lesion.

BRIEF DESCRIPTION OF THE DRAWINGS

The invention will be described below, with reference to the enclosed drawings, given by way of example of possible embodiments of the invention and in which.

DESCRIPTION OF THE INVENTION

Figures 1A, 1B, 1C:
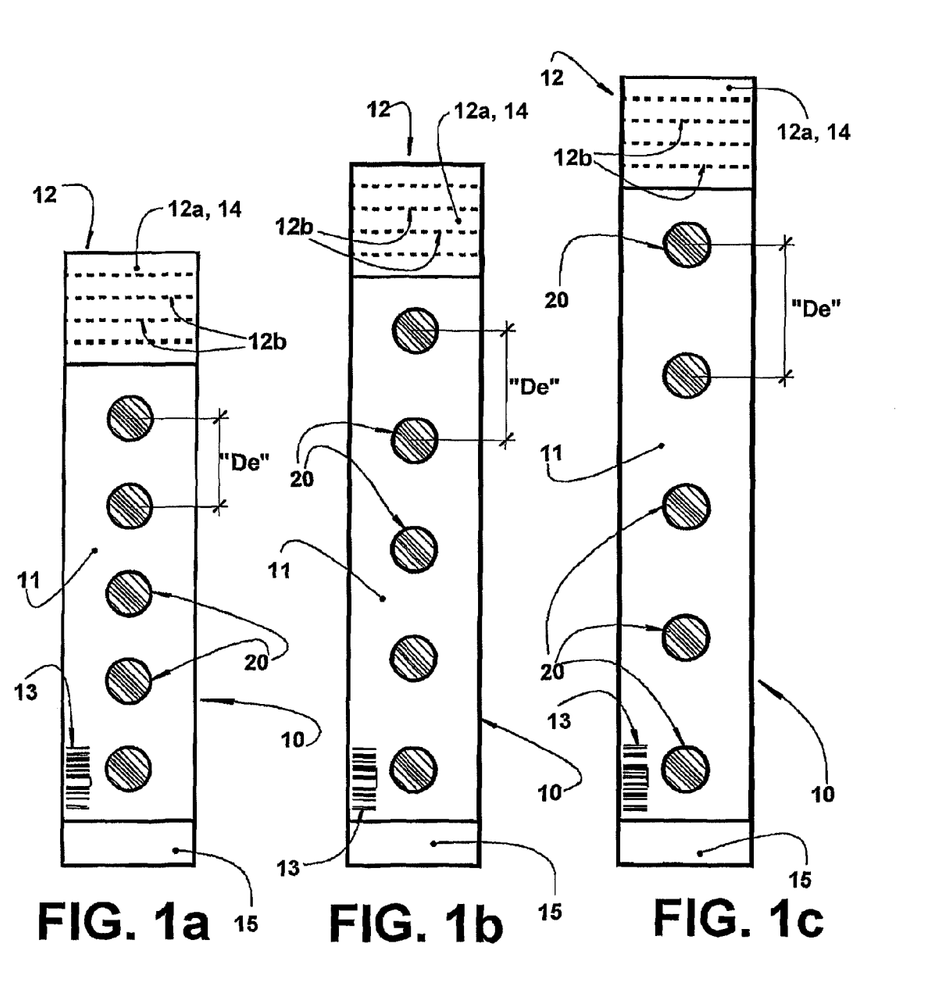
FIGS. 1a, 1b and 1c illustrate schematic lower plan views of three different lengths of electrode modules, presenting the same number of electrodes, equally spaced from one another in each module, but by different and specific distances for each module.

FIGS. 1a, 1b and 1c illustrate three electrode modules 10, each comprising a respective extension of support strap 11 constructed in any suitable material that presents flexibility without, however, presenting elastic deformation in the longitudinal direction. In the figures each electrode module 10 presents a determined length different from that of the other electrode modules 10, each module comprising the same number of five electrodes 20 equidistant from one another by a certain distance "De", which generally varies between the electrode modules 10.

Figures 2A, 2B:
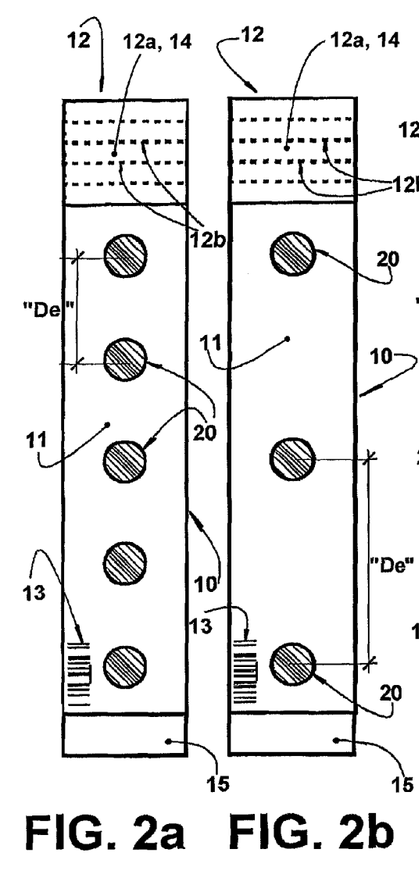
FIGS. 2a and 2b illustrate schematic lower plan views of two electrode modules with the same length, but containing different numbers of electrodes.

Thus, the electrodes 20 of the support strap 11 of smaller length are equally spaced, but with a distribution according to which the electrodes 20 are closer to each other in relation to the mutual spacing of the electrodes 20 from the other two electrode modules 10. FIGS. 2a and 2b illustrate two electrode modules 10 formed by support straps 11 of the same length, one of the modules carrying five electrodes 20, while the other carries only three electrodes 20 that keep from one another a distance "De" greater than that of the electrodes 20 of the other electrode module 10.

Figures 3A, 3B:
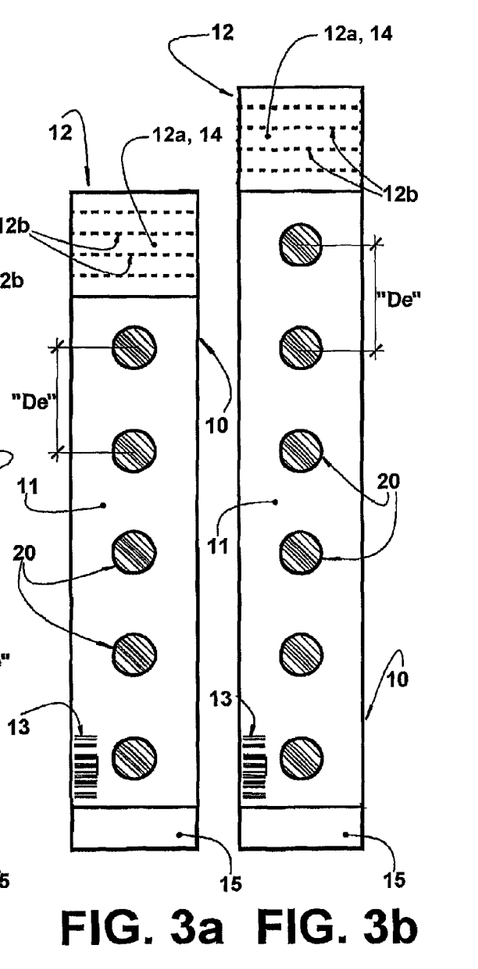
FIGS. 3a and 3b illustrate schematic lower plan views of two electrode modules with different lengths and with different numbers of electrodes in each of them, but the electrodes of the two modules being equally spaced apart by the same distance.

FIGS. 3a and 3b illustrate two more examples of electrode modules 10 presenting support straps 11 with different lengths, the electrode modules 10 presenting different numbers of electrodes 20 but being equally spaced apart.

Figures 4, 5A, 5B:
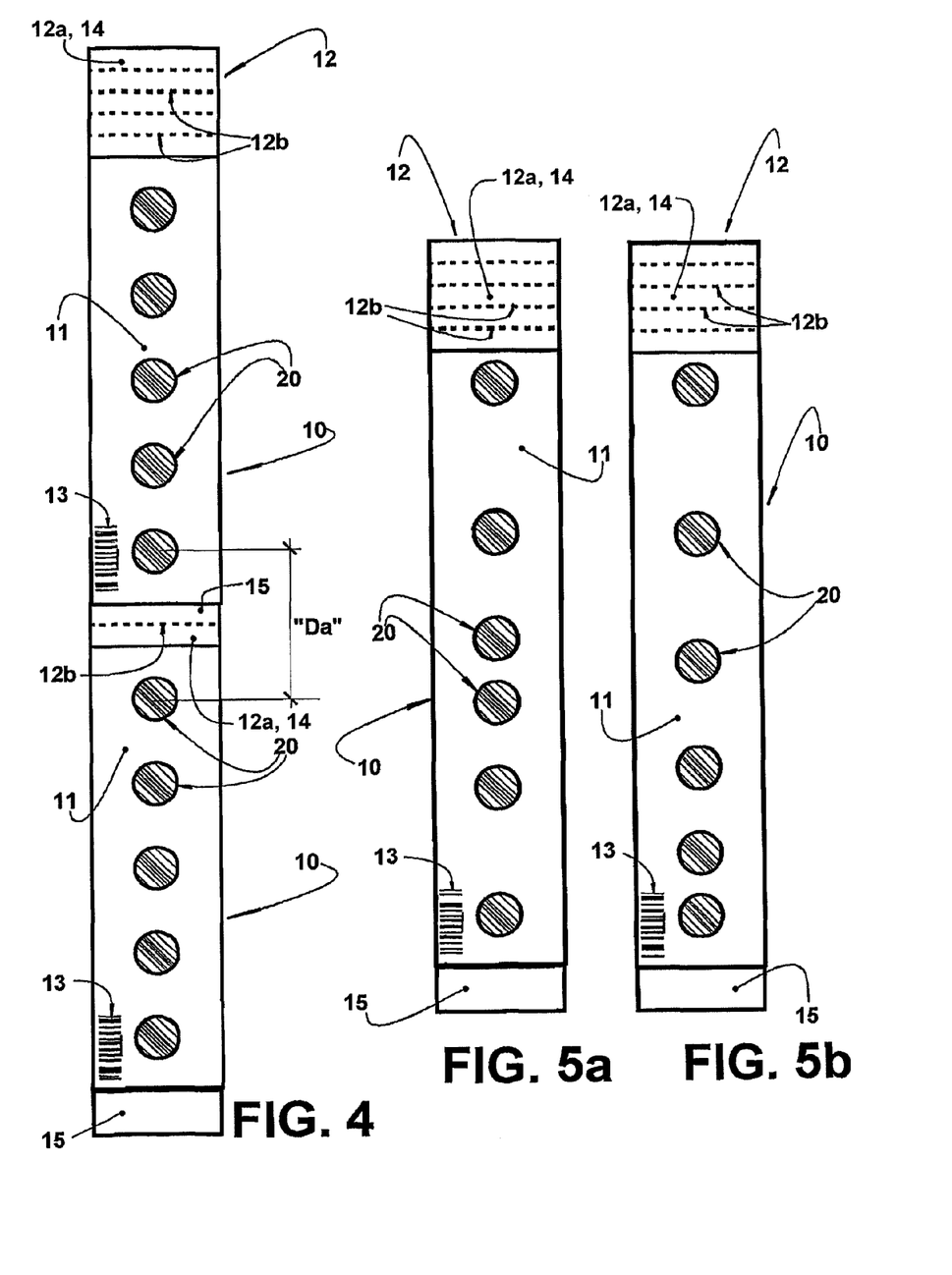
FIG. 4 represents a schematic lower plan view of the two electrode modules longitudinally coupled to each other to form an electrode belt extension.
FIGS. 5a and 5b illustrate schematic lower plan views of two electrode modules with the same length and number of electrodes, but with the latter being arranged in different manners regarding the distribution along the support strap.

FIG. 4 represents an electrode belt extension defined by the longitudinal junction of the two support straps 11, the electrode belt extension being dimensioned to cover a respective extension of a body segment C of the patient.

As further discussed below, the different electrode modules 10 are dimensioned in extension, number and distribution of electrodes 20 to comply with different conditions of application to the body to be analyzed. It should be understood that the electrode modules 10 can be applied and spaced from one another along the same plane of interest sectioning the body segment C, or even in generally parallel different planes, so as to produce a three-dimensional image of the body section being analyzed.

In the situations in which the electrode modules 10 are applied to the same plane, the electrode modules 10 can be provided with a positioning means 12 which, as illustrated in FIGS. 1a-5b, takes the form of a prolongation 12a incorporated into one of the ends of the support strap 11 and provided with marks 12b that allow determining the spacing distance "Da" between two adjacent electrodes 20 for each two consecutive electrode modules 10. In determined circumstances, the different electrode modules 10 can be coupled longitudinally to one another, through their adjacent ends (see FIG. 4). In this case, one of the ends of each support strap 11 can incorporate, in the longitudinal direction, a coupling means 14 constructed in different ways such as, for example, a strap made of a hook and loop material known by the brand name VELCRO®. The other end of each support strap 11 carries a coupling receiving means 15 schematically illustrated in the drawings and which is constructed to receive and interlock the coupling means 14 of another electrode module 10. Thus, the coupling receiving means 15 can take the form of a strap made of an adhesive material to be adhered to the coupling means 14.

In the embodiment illustrated in FIGS. 1a-5b, the coupling means 14 is defined in the positioning means 12 itself of the support strap 11, mingling with the respective prolongation 12a of the support strap 11. However, it should be understood that the coupling means 14 is not obligatorily constructed in conjunction with the positioning means 12.

As discussed below, each electrode module 10 may contain, in its support strap 11, an individual identification code 13 that can take the form of a bar code or an alphanumeric identification. The reading of the individual identification code 13 allows determination of the longitudinal extension of the module 10, the number of electrodes 20 and the arrangement of the electrodes 20 along the extension of the support strap 11, since the arrangement of the modules 10 on each respective support strap 11 can vary from module 10 to module 10, as illustrated in FIGS. 5a and 5b.

It should be understood that the provision of the individual identification codes 13 of the support straps 11 is not obligatory, since the number of electrodes 20, the distance "De" between the electrodes 20 of each electrode module 10 and the spacing distance "Da" between each two consecutive electrode modules 10 can be measured and informed to a monitoring apparatus (not illustrated), before starting the tomography.

Considering the possibility of providing electrode modules 10 presenting more concentrated or more disperse arrangements of electrodes 20 on the respective support straps 11, the operator can select the more suitable electrode modules 10 to provide a sharper image of a determined region of interest of the body segment C. In the regions of less interest, an electrode module 10 with a smaller number of electrodes 20 can be used, while in the regions of greater interest, one can use electrode modules 10 containing a higher concentration of electrodes 20 or even a localized concentration of electrodes 20, as illustrated in FIGS. 5a and 5b. The electrode modules 10 can be longitudinally coupled to each other or only seated against the body segment C, according to different combinations of number and concentration of electrodes 20. The fixation of the support straps 11 against the body segment C of the patient can be effected in different manners, with or without the assistance of the auxiliary positioning belt. The support straps 11 of each electrode module 10 can be built in any suitable electrically non-conductive material such as, for example, non-woven fabric, foam and polymers that impart characteristics of flexibility to the support straps 11.

Figure 6A:
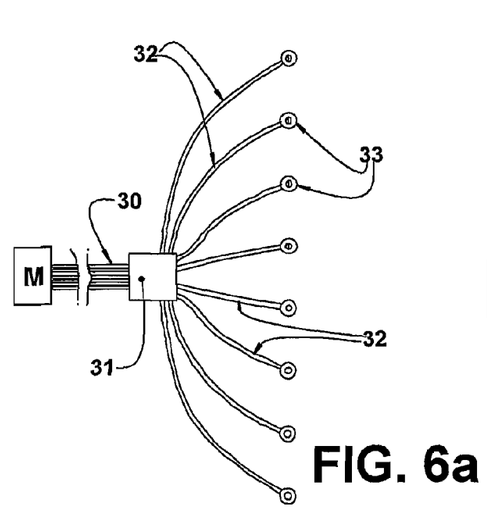
FIGS. 6a and 6b represent schematic plan view of two different arrangements of electrical conducting cables with the respective end connectors.
Figure 6B:
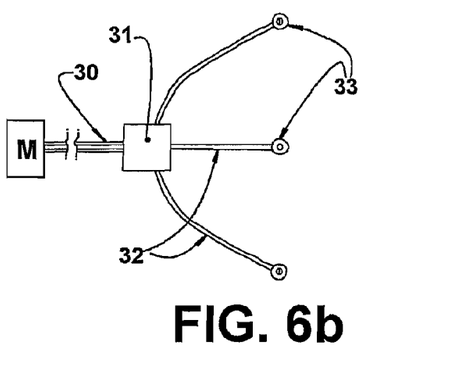
Figure 12:
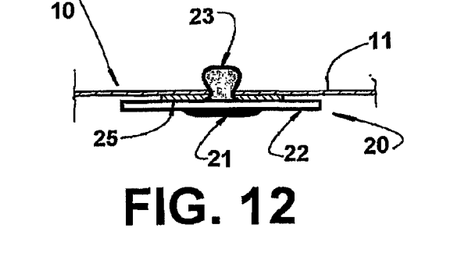
FIG. 12 represents a diametrical sectional view of an electrode mounted through a respective hole of the support strap of FIG. 11.
Figures 13, 14:
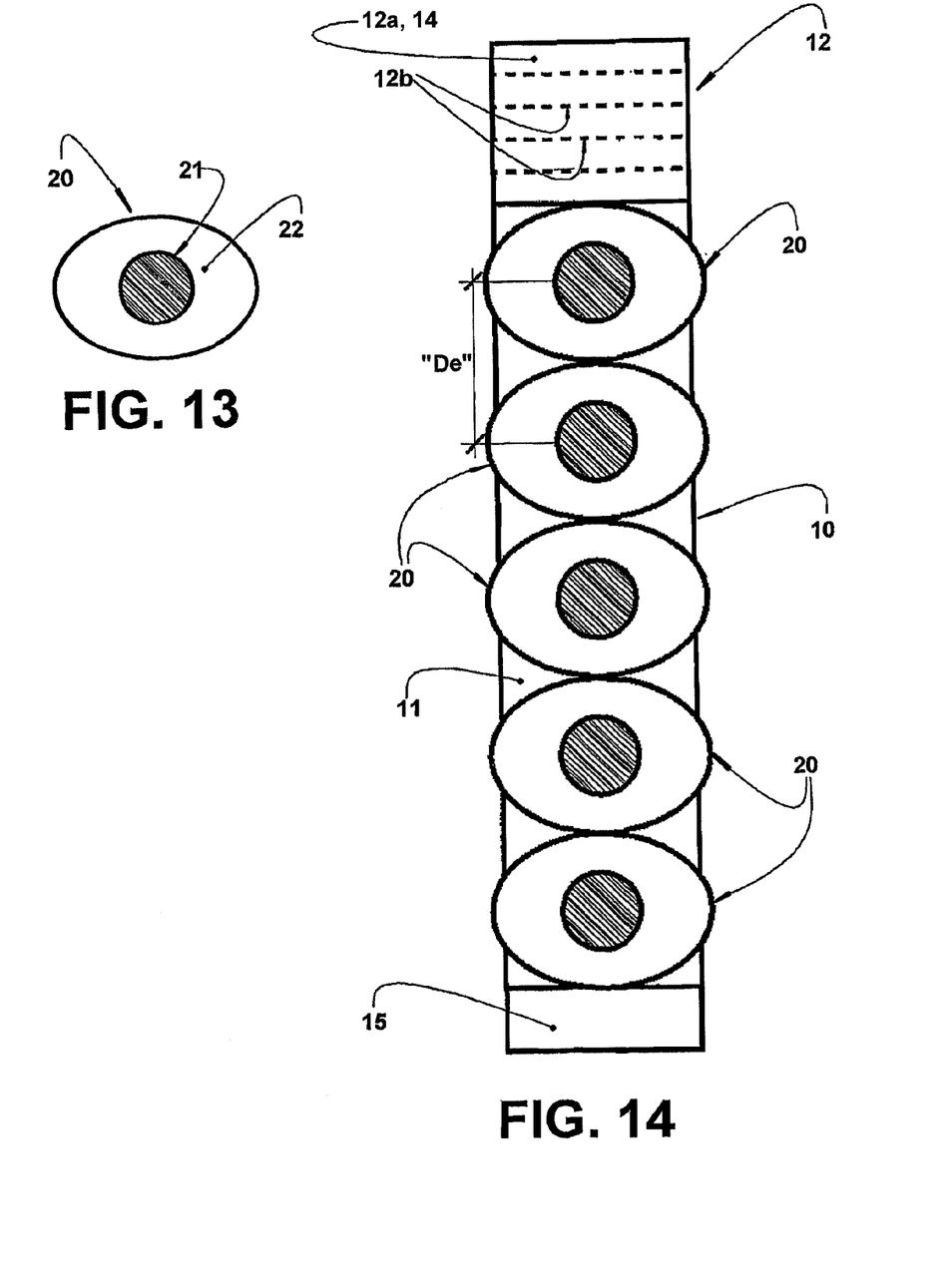
FIG. 13 represents a lower plan view of the electrode of FIG. 12.
FIG. 14 represents a lower plan view of the support strap of FIG. 11, carrying an electrode in each hole.

Although not being illustrated and described in details herein, since it is not the object of the invention, each electrode 20 can be constructed in different ways, known or unknown in the prior art, as long as they present, as exemplified in FIGS. 12, 13 and 14, a contact portion 21 surrounded by a seating ring 22 and to be seated against the body segment C, and a connecting portion 23 projecting upwardly from the support strap 11 and configured to receive and retain an end connector of a respective electrical conducting cable 30 arranged to connect each electrode 20 to a monitoring apparatus M, schematically represented in FIGS. 6a and 6b.

FIGS. 6a and 6b illustrate two different arrangements of electrical conducting cables 30, which after passing together through a distribution box 31, are distributed in respective connecting legs 32, whose free ends carry, each one, a respective connector 33 to be releasably coupled to the connecting portion of a respective electrode 20. Due to the flexibility of the connecting legs 32 of the electrical conducting cables 30, they can be utilized for adapting the electrical conducting cables 30 of electrode modules with different lengths and distribution arrangements of electrodes 20.

Figure 7:
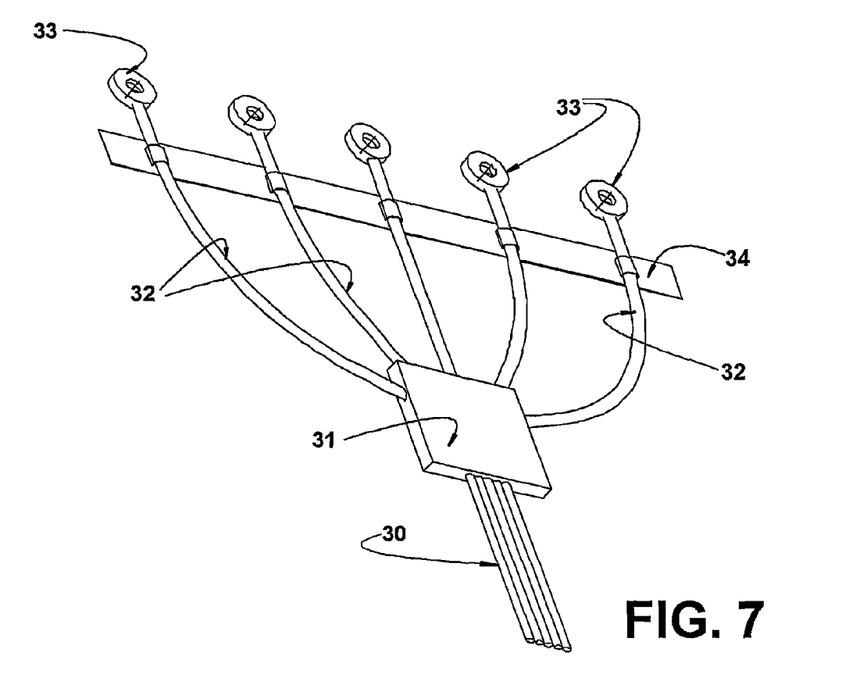
FIG. 7 represents a rather schematic perspective view of another arrangement of electrical conducting cables with the respective end connectors.
Figure 8:
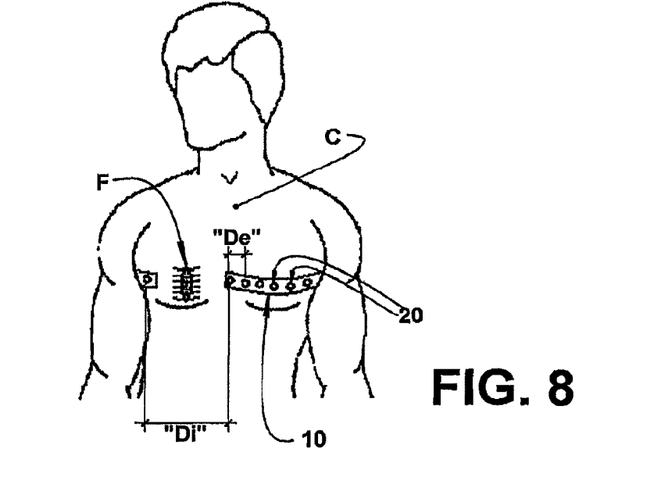
FIG. 8 represents a frontal view of a patient's torso, to which is applied a plurality of electrodes, which are spaced apart by a distance that may vary along the contour of the body segment, an interruption being provided in the sequence of electrode modules in the frontal region of the thorax in which there is an injury, the interruption defining a certain interruption distance between the electrodes adjacent to the interruption and pertaining to the two spaced apart modules.
Figure 8A:
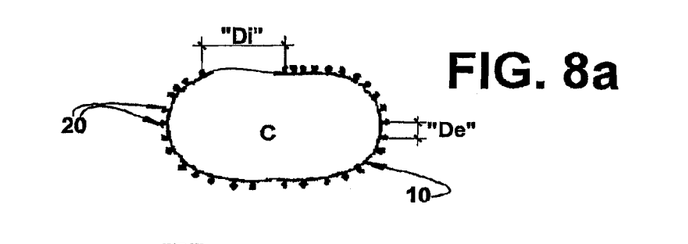
FIG. 8a represents a simplified cross-sectional view of the body torso illustrated in FIG. 8, showing the arrangement of thirty-one electrodes around the body segment, taken according to line A-A in FIG. 8.
Figure 8B:
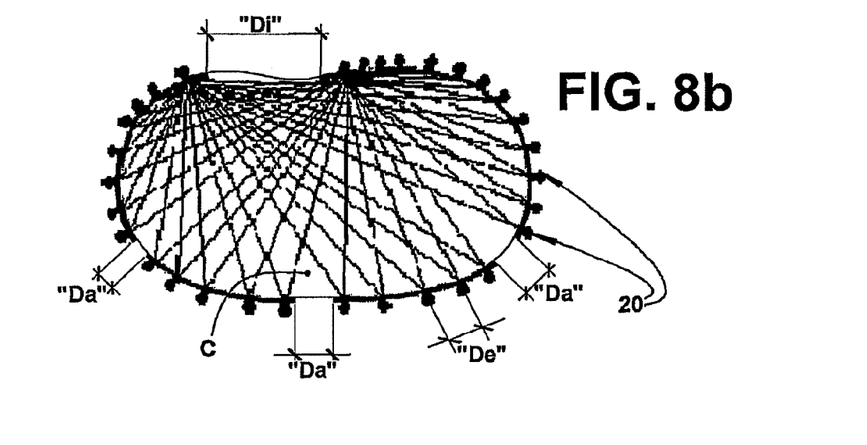
FIG. 8b is a view similar to that of FIG. 8a, but schematically illustrating the arrangement of the electrodes in the finite element mesh upon which the operation of the image reconstruction algorithm is based.

In FIG. 7 is illustrated an arrangement of five connecting legs 32, projecting outwardly from a distribution box 31, for having in the end portions thereof and retained, at predetermined spacings, a positioning plate 34 which maintains the connectors 33 in a predetermined positioning. In this case, the positioning plate 34 makes the arrangement of electrical conducting cables 30 be designed to a certain specific type of electrode module 10, facilitating to mount the connecting legs 32 in the connecting portions of the electrodes 20 of the respective electrode module 10. FIGS. 8, 8a and 8b illustrate the application of electrode modules in a body segment C defined by the thorax of the patient who presents an injury F in the right region of his chest. In order to avoid placing electrodes 20 in the injured region of the patient, the arrangement of electrode modules 10 around the body segment C presents an interruption, making the two electrodes 20 adjacent to the interruption define therebetween an interruption distance "Di" sufficient to set free the region of the injury F. The electrode distribution in the arrangement of these figures follows a different distance pattern "De" between the electrodes 20, making possible to observe a greater concentration of the electrodes in the frontal left region of the body segment C (FIG. 8a). FIG. 8b illustrates the operational mode of the image reconstruction algorithm based upon the insertion of the actual arrangement of the electrodes 20 in the finite element mesh. The thorax image resolution of the injury region will be different in case the electrodes 20 are positioned in an equidistant way.

An interesting aspect of the model based on the finite element mesh is that the distance "De", "Da" or "Di" between the electrodes 20 of the same module and of different modules needs only to be informed to the monitoring M apparatus, and not required to be constant. FIGS. 9a, 9b, 9c, 9d, 9e and 9f illustrate different combinations of electrode modules 10 surrounding a body segment C.

Figure 9A:
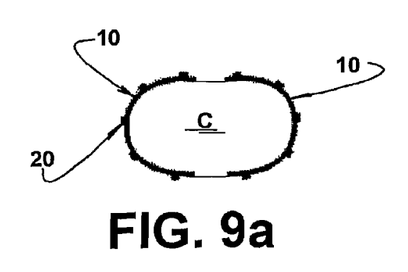
FIGS. 9a, 9b, 9c, 9d, 9e and 9f are views similar to that of FIG. 8a, but illustrating different combinations of the electrode modules to surround the body segment illustrated in cross section, some of the modules presenting the same number of electrodes and the same distance between the electrodes.
Figure 9B:
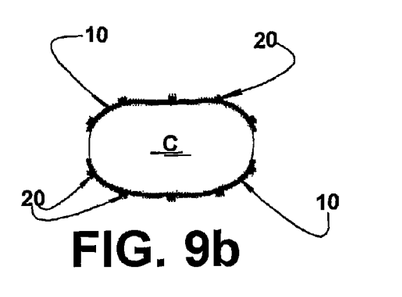
Figure 9C:
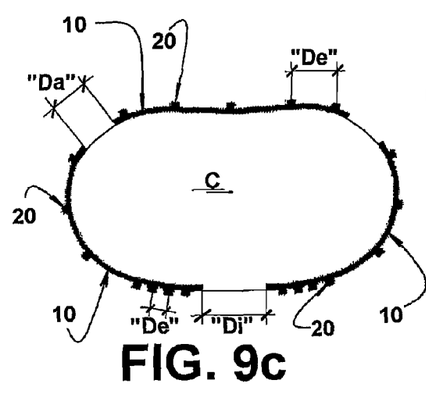
Figure 9D:
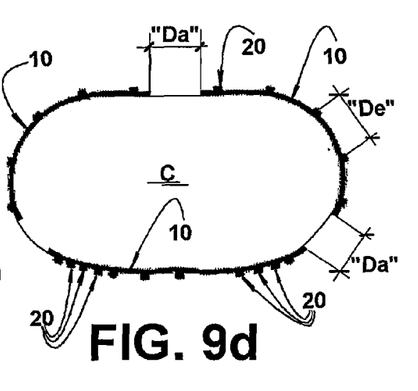

FIG. 9a illustrates the positioning of a pair of electrode modules 10 around a body segment C of a newborn child presenting a thorax of about 25 cm of perimeter, the two electrode modules 10 being identical. FIG. 9b illustrates a positioning different from that presented in FIG. 9a, but also utilizing a pair of electrode modules 10 of the same construction. FIGS. 9c and 9d illustrate two different arrangements containing three electrode modules 10 disposed around a body segment C, the electrodes of the modules presenting different number and distribution.

Figure 9E:
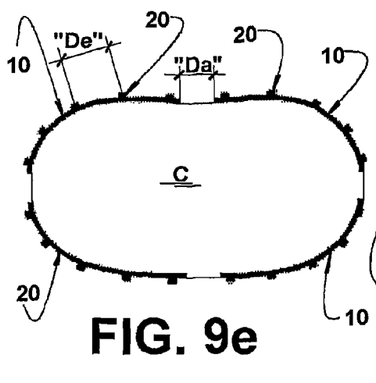
Figure 9F:
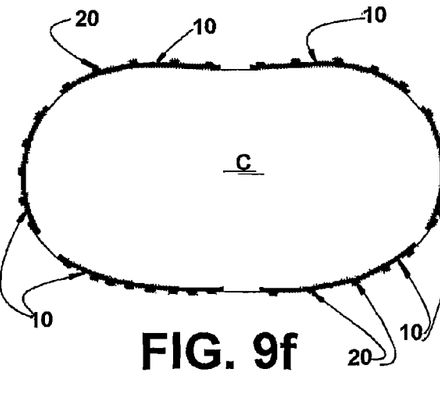

FIGS. 9e and 9f illustrate the utilization of four and six electrode modules 10, respectively, the electrodes 20 of the modules 10 of FIG. 9e being provided with the same number and equidistantly disposed. FIG. 9f illustrates the arrangement of electrode modules 10 around an adult thorax of about 80 cm of perimeter, with one of the modules differing from the others by the number and by the distance between the electrodes 20.

The constructions of electrode modules 10 described above refer to embodiments in which each module 10 is formed by an extension of support strap 11, previously sectioned to a pattern length predetermined for that module 10, and in which it is mounted an also predetermined and standardized number of electrodes 20 disposed according to equal or different, but also predetermined, distances "De".

Figure 10:
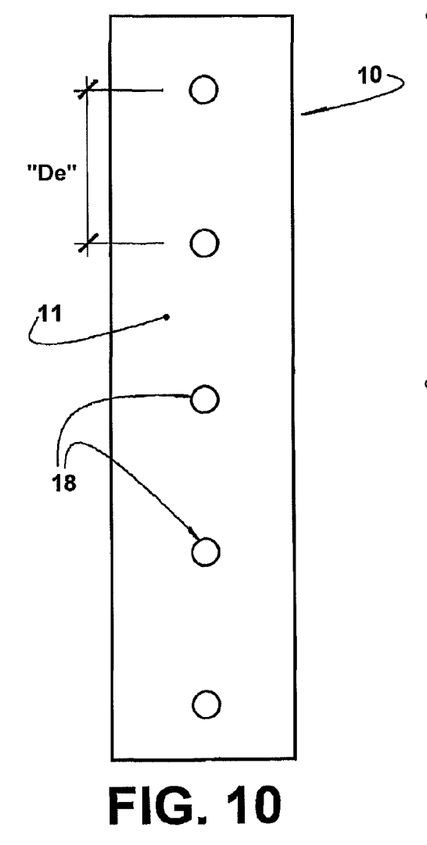
FIG. 10 represents a plan view of a support strap extension provided with holes disposed according to a median longitudinal alignment, an electrode being then mounted in at least one of the holes.
Figure 15:
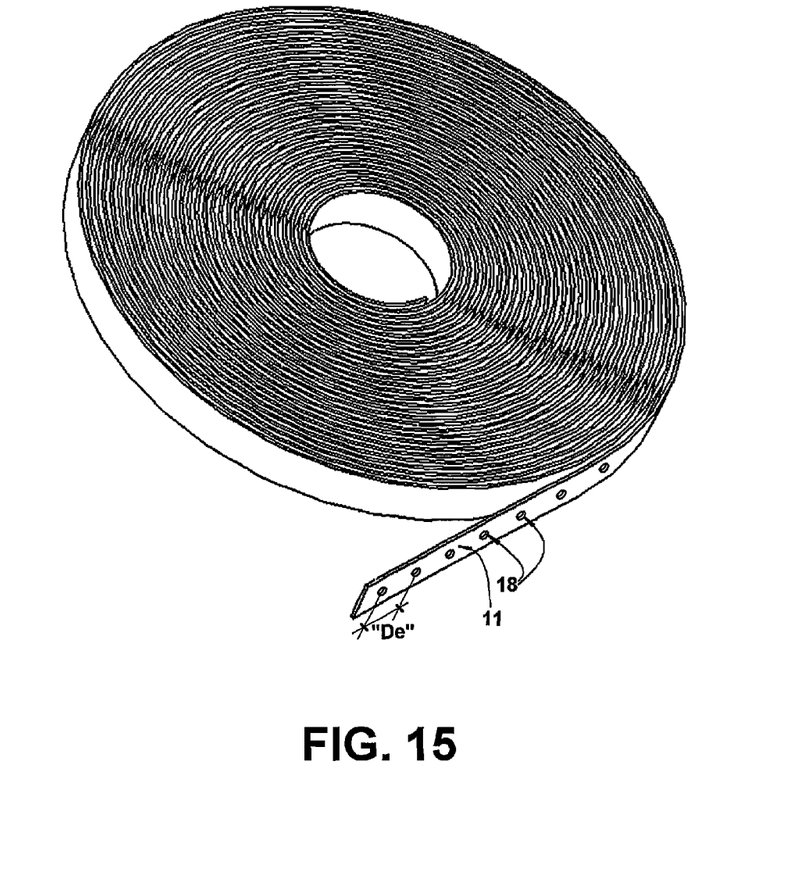
FIG. 15 represents a perspective view of a continuous support strap provided with a median longitudinal alignment of holes and illustratively shown in the form of a coil.

However, as illustrated in FIG. 10, each electrode module 10, can be formed by the operator himself, or by the EIT application staff, from an extension of support strap 11 sectioned from a continuous strap, which can be provided, for example, in a coil as illustrated in FIG. 15. A continuous support strap 11 is provided with a median longitudinal alignment of holes 18 spaced from one another by the same distance "De" that can correspond to the minimum possible distance "De" between two electrodes 20 or a distance "De" predetermined as a basic pattern of concentration of the electrodes 20 in an extension of the body segment C to be analyzed.

After defining the extension of the module support strap 11 to be formed, the operator can secure the electrodes 20 in the holes 18 of the support strap 11.

Figure 11:
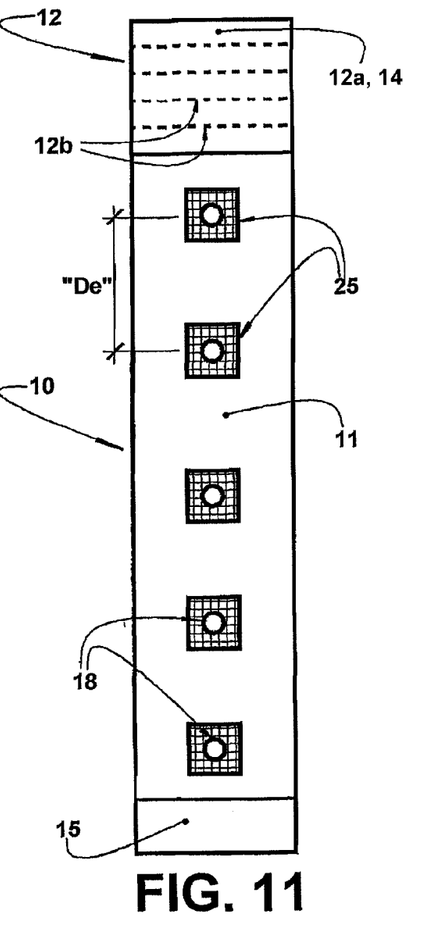
FIG. 11 represents a lower plan view of a support strap extension similar to that of FIG. 10, but carrying coupling means and coupling receiving means in its ends and also elements for retaining the electrodes around the holes of the support strap.

The extension of support strap 11 illustrated in FIGS. 10, 11 and 14, presents five holes 18, and each can receive a respective electrode 20. In the example of FIGS. 11 and 14, each of the five holes 18 of the support strap 11 receives an electrode 20. However, it should be understood that the electrodes 20 can be mounted in only one or some of the holes 18, depending on the operational pattern to be obtained by the module 10 to be formed.

In the case the extension of support strap 11 is sectioned from a continuous strap previously provided with the holes 18, each extension of support strap 11 usually does not incorporate the positioning means 12, the coupling means 14 and the coupling receiving means 15, as illustrated in FIG. 10. Nevertheless, as illustrated in FIGS. 11 and 14, the extensions of the already perforated support strap 11 can receive and secure, in their opposite ends, by any suitable process, a positioning means 12, a coupling means 14 and a coupling receiving means 15.

It should be further understood that the continuous support strap 11 can be supplied to the EIT system operator already with the electrodes 20 mounted in the holes 18 of the support strap 11. In this case, there should be provided different patterns of continuous support straps 11, each pattern defining a particular distance "De" for the electrodes 20, but allowing the operator to select the number of electrodes 20 in each desired module.

FIG. 11 illustrates an extension of support strap 11 under which is applied, around each hole 18 that will receive a respective electrode 20, an adhesive element 25 which can be defined by an annular portion of a double-face adhesive tape. The adhesive element 25 retains the seating ring 22 of an electrode 20 against the lower face of the support strap 11, while the connecting portion 23 of the electrode 20 is fitted through the respective hole 18, projecting upwardly from the upper face of the support strap 11 to be coupled to an electrical conducting cable 30.

Figure 16:
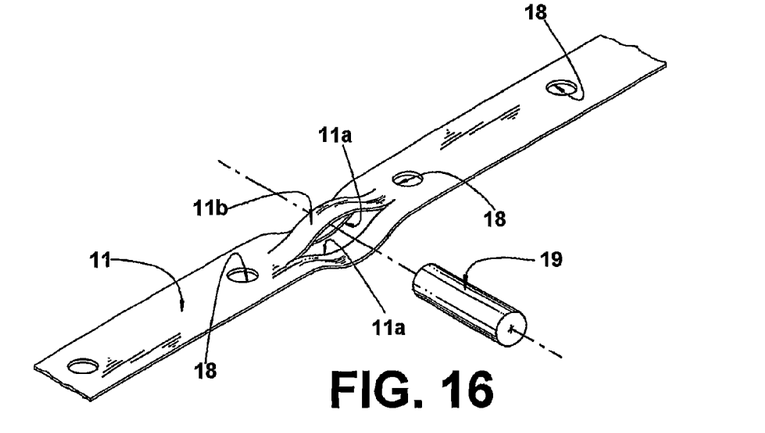
FIG. 16 represents a perspective view of a strap extension for the formation of an electrode module presenting a construction which allows adjusting it to the longitudinal extension of each support strap.

As it can be noted in FIG. 16 of the enclosed drawings, each extension of support strap 11 can be provided between each two consecutive electrodes 20 or between each two consecutive holes 18 for the subsequent mounting of respective electrodes 20, with a pair of longitudinal parallel slots 11a which are spaced from one another and from the adjacent longitudinal lateral edges of the extension of support strap 11.

FIG. 16 illustrates an extension of support strap 11 of the type illustrated in FIG. 10, i.e., an extension of support strap 11 sectioned from a continuous strap or otherwise produced and presenting only the holes 18 for placing the electrodes, but without the latter, for better visualizing the constructive alternative proposed herein. In this constructive alternative of FIG. 16, each two slots 11a of the extension of support strap 11 define a median lug 11b incorporated by its ends into the strap itself, only one of these lugs 11b being deformed by inserting a spacer 19 between a lug 11b and the adjacent lateral portions of the support strap 11, making both the lug 11b and the adjacent region of the support strap 11 be deformed to reduce the extension of the support strap 11.

In this way, there is obtained an extremely simple constructive solution which allows the support strap 11 to be easily and quickly adapted along the circumferential extension of a body segment C of the patient. The placement of the extension of the support strap 11 on a body segment C of the patient, with one or more lugs 11b being deformed by a respective spacer 19, can be thus effected with the support strap 11 presenting a dimension that is more or less contracted as a function of the number of spacers 19 adapted under the respective lugs 11b. After the adaptation of the support straps 11, the spacers 19 can be removed to permit the support straps 11 to present a longitudinal extension adequate to the circumferential extension of the body segment C, considering the patient's respiratory movements.

It should be further understood that the spacers 19 can be placed to provide a dimensional adjustment for reducing the longitudinal extension of each support strap, to better adjust it to a reduction in the contour of the body segment C, after the strap has been applied under an anomalous respiratory condition or body volume condition.

Figure 17:
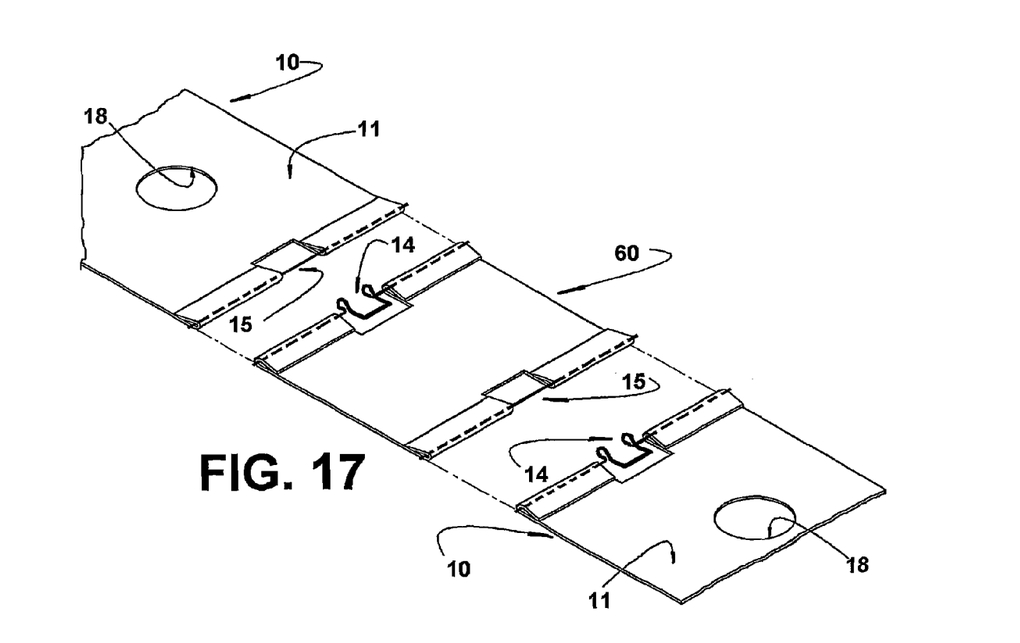
FIG. 17 represents a partially sectioned perspective view of an assembly comprising two support straps of the type illustrated in FIG. 10 and provided with coupling means and end coupling receiving means, as well as a connecting module for interconnecting the two support straps.

As illustrated in FIG. 17, two consecutive support straps 11 can be connected to each other by means of a connecting module 60, generally defined by an extension of support strap made of a material identical to the one used in the support straps 11 which define the electrode modules, or also constructed in any suitable material, the connecting modules 60 being dimensioned to provide a certain predetermined distance with different values between two consecutive support straps 11, each connecting module 60 being further provided, in their opposite ends, with a coupling means 14 and a coupling receiving means 15 constructed to mate with the coupling means 14 and coupling receiving means 15 provided in the support straps 11.

In the illustrated configuration, the coupling means 14 and the coupling receiving means 15 respectively take the form of small hooks and rods, which are mutually connected upon uniting two extensions of support strap 11, directly or by using an intermediate connecting module 60.

As described above, the electrode assembly disclosed by the present invention provides the EIT system operator with different electrode modules constructed to provide specific operational patterns in the system, the patterns being predetermined in the project of the modules, in order to allow the latter to comply with the different conditions of application and diagnosis.

The invention claimed is:

1. An electrode assembly for electrical impedance tomography (EIT), the electrode assembly comprising:
    an electrode belt having a plurality of EIT electrode modules configured to couple together longitudinally and configured to couple with an EIT monitoring apparatus configured to generate an EIT image responsive to signals received the plurality of EIT electrode modules, wherein each EIT electrode module of the plurality of EIT electrode modules includes:
        a support strap having a first end with a coupling element and a second end with a coupling receiving element, wherein the coupling element of one EIT electrode module is configured to couple longitudinally with the coupling receiving element of another EIT electrode module to form the electrode belt; and
        EIT measurement electrodes attached to the support strap in respective fixed positions;
    wherein at least two EIT electrode modules of the plurality of EIT electrode modules of the same electrode belt have a different spacing of the EIT measurement electrodes for a non-uniform distribution of the EIT measurement electrodes along at least a portion of the electrode belt.

2. The electrode assembly of claim 1, wherein at least two EIT electrode modules of the plurality of EIT electrode modules of the same electrode belt have a same spacing of the EIT measurement electrodes for a uniform distribution of the EIT measurement electrodes along at least another portion of the electrode belt.

3. The electrode assembly of claim 1, wherein the at least two EIT electrode modules have a different number of EIT measurement electrodes attached to the respective support strap.

4. The electrode assembly of claim 1, wherein the at least two EIT electrode modules have a same number of EIT measurement electrodes attached to the respective support strap.

5. The electrode assembly of claim 1, wherein each EIT electrode module of the plurality of electrode modules further includes an individual identification code configured to identify the characteristics of its corresponding EIT electrode module.

6. The electrode assembly of claim 5, wherein the identification code is a bar code.

7. The electrode assembly of claim 5, wherein the characteristics identified by the individual identification codes include a distance between each EIT measurement electrode with its adjacent EIT measurement electrode of the EIT electrode module.

8. The electrode assembly of claim 1, wherein the support strap of each electrode module of the plurality of electrode modules includes a positioning element in one of the ends of the respective support strap.

9. The electrode assembly of claim 8, wherein each positioning element comprises an extension of one end of the respective support strap provided with marks indicative of the relative positioning between two coupled electrode modules.

10. The electrode assembly of claim 1, wherein the coupling element is combined with a positioning element.

11. The electrode assembly of claim 1, wherein each support strap is provided, between the positions of each two consecutive EIT measurement electrodes, with a pair of longitudinal slots, each longitudinal slot of the pair placed between the median line of the support strap and its lateral edges, defining therebetween a lug selectively deformable outwardly from the plane of an adjacent lateral region of the support strap upon the introduction of a spacer between a lower face of the lug and an upper face of the adjacent lateral regions of the support strap.

12. The electrode assembly of claim 1, wherein the coupling element includes a rod that is bent in the form of a hook that engages the coupling receiving element that includes a straight rod.

13. The electrode assembly of claim 1, wherein the electrode belt has a discontinuity having an interruption distance between at least two EIT electrode modules of the plurality of EIT electrode modules.

14. The electrode assembly of claim 1, wherein the support strap is constructed of a flexible material which does not present elastic deformation of the support strap in the longitudinal direction.

15. The electrode assembly of claim 1, wherein at least one EIT electrode module includes EIT measurement electrodes that are concentrated in at least one region and dispersed in at least one other region relative to each other.

16. The electrode assembly of claim 1, further comprising a plurality of connecting legs configured to receive a distributed arrangement of conduction cables, wherein the plurality of connecting legs are flexible to manipulate such that the respective connecting legs are releasably coupled with the EIT measurement electrodes of the electrode belt having the different spacing.

17. An electrical impedance tomography (EIT) monitoring system, the EIT monitoring system comprising:
a display; and
an EIT processor operably coupled with the display, the EIT processor configured to:
couple with an electrode belt having a plurality of EIT electrode modules, wherein each EIT electrode module of the plurality of EIT electrode modules includes:
a support strap having a first end with a coupling element and a second end with a coupling receiving element, wherein the coupling element of one EIT electrode module is configured to couple longitudinally with the coupling receiving element of another EIT electrode module to form the electrode belt; and
EIT measurement electrodes attached to the support strap in respective fixed positions, wherein at least two EIT electrode modules of the plurality of EIT electrode modules of the same electrode belt have a different spacing of the EIT measurement electrodes for a non-uniform distribution of the EIT measurement electrodes along at least a portion of the electrode belt; and
generate an EIT image responsive to signals received from the plurality of EIT electrode modules using spacing information of the EIT measurement electrodes of each EIT electrode module.

18. The EIT monitoring system of claim 17, wherein the processor is further configured to receive the spacing information from an identification code on each EIT electrode module.

19. The EIT monitoring system of claim 17, wherein the EIT image exhibits a resolution that is greater at locations corresponding to a more concentrated number of EIT electrodes relative to locations corresponding to a less concentrated number of EIT electrodes of the electrode belt.

20. A method for forming an electrode assembly for an electrical impedance tomography (EIT) system, the method comprising:
forming a plurality of EIT electrode modules by attaching a plurality of EIT measurement electrodes in respective fixed positions with a plurality of support straps, each support strap having at least one electrode attached thereto, wherein at least two EIT electrode modules of the plurality of EIT electrode modules have different spacing of the EIT measurement electrodes; and
coupling the plurality of EIT electrode modules having the different spacing to form at least part of an electrode belt for a non-uniform distribution of the EIT measurement electrodes along at least a portion of the electrode belt.

21. The method of claim 20, wherein the non-uniform distribution includes a relatively more concentrated arrangement of EIT measurement electrodes on a first EIT electrode module corresponding to a region of interest and a relatively more disperse arrangement of EIT measurement electrodes on a second EIT electrode module corresponding to a region of less interest.

22. The method of claim 20, wherein coupling the plurality of EIT electrode modules forms an electrode belt that is continuous when arranged on a patient.

23. The method of claim 20, wherein coupling the plurality of EIT electrode modules forms an electrode belt that is discontinuous when arranged on a patient.

* * * * *